(12) United States Patent
Wang et al.

(10) Patent No.: US 10,772,821 B2
(45) Date of Patent: Sep. 15, 2020

(54) ORAL COMPOSITIONS

(71) Applicant: 3M Innovative Properties Company, St. Paul, MN (US)

(72) Inventors: Yizhong Wang, Woodbury, MN (US); Joel D. Oxman, Minneapolis, MN (US); Tiffany Ton, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/585,341

(22) Filed: Sep. 27, 2019

(65) Prior Publication Data

US 2020/0022896 A1 Jan. 23, 2020

Related U.S. Application Data

(63) Continuation of application No. 14/917,442, filed as application No. PCT/US2014/054074 on Sep. 4, 2014, now abandoned.

(60) Provisional application No. 61/876,441, filed on Sep. 11, 2013.

(51) Int. Cl.
*A61K 8/81* (2006.01)
*A61Q 11/00* (2006.01)

(52) U.S. Cl.
CPC .......... *A61K 8/8141* (2013.01); *A61K 8/8152* (2013.01); *A61Q 11/00* (2013.01); *A61K 2800/42* (2013.01); *A61K 2800/52* (2013.01); *A61K 2800/5426* (2013.01); *A61K 2800/92* (2013.01)

(58) Field of Classification Search
CPC .............................. C08F 20/10; A61K 6/0067
USPC .......................................... 524/556; 424/443
See application file for complete search history.

(56) References Cited

U.S. PATENT DOCUMENTS

| | | | |
|---|---|---|---|
| 4,134,935 A | 1/1979 | Quiring | |
| 4,876,092 A | 10/1989 | Mizobuchi | |
| 4,883,534 A | 11/1989 | Sandham | |
| 5,160,737 A | 11/1992 | Friedman | |
| 5,249,206 A | 9/1993 | Applebaum | |
| 5,330,746 A | 7/1994 | Friedman | |
| 5,438,076 A | 8/1995 | Friedman | |
| 5,456,745 A | 10/1995 | Roreger | |
| 5,521,293 A | 5/1996 | Vermeer | |
| 5,639,795 A | 6/1997 | Friedman | |
| 5,776,435 A | 7/1998 | Gaffar | |
| 6,177,097 B1 | 1/2001 | Hanke | |
| 6,485,709 B2 | 11/2002 | Banerjee | |
| 6,770,266 B2 | 8/2004 | Santarpia, III | |
| 6,854,973 B2 | 2/2005 | Butcher | |
| 8,840,918 B2 | 9/2014 | Singh | |
| 2003/0183124 A1 | 10/2003 | Engelbrecht | |
| 2004/0126333 A1 | 7/2004 | Galli | |
| 2004/0258723 A1 | 12/2004 | Singh | |
| 2005/0063921 A1 | 3/2005 | Charmot | |
| 2005/0113510 A1* | 5/2005 | Feldstein | ............ A61K 6/0067 524/556 |
| 2005/0196358 A1 | 9/2005 | Georgiades | |
| 2005/0215727 A1 | 9/2005 | Feldstein | |
| 2006/0004120 A1 | 1/2006 | Orlowski | |
| 2006/0024246 A1 | 2/2006 | Maitra | |
| 2008/0299520 A1 | 12/2008 | Ali | |
| 2009/0191279 A1 | 7/2009 | Kennard | |
| 2009/0257961 A1 | 10/2009 | Deng | |
| 2009/0324516 A1 | 12/2009 | Muscle | |
| 2011/0250557 A1 | 10/2011 | Qian | |
| 2012/0288566 A1 | 11/2012 | Friedman | |
| 2013/0052146 A1 | 2/2013 | Yang | |

FOREIGN PATENT DOCUMENTS

| | | |
|---|---|---|
| EP | 0404558 | 12/1990 |
| JP | 61-289006 | 12/1986 |
| JP | 3-022039 | 1/2000 |
| JP | 3-590438 | 8/2004 |
| WO | WO 1994-04126 | 3/1994 |
| WO | WO 2009-150596 | 12/2009 |
| WO | WO 2011/042897 | 4/2011 |
| WO | WO 2011-084673 | 7/2011 |
| WO | WO 2011-162965 | 12/2011 |

(Continued)

OTHER PUBLICATIONS

Jonier, "The bleaching of teeth: A review of literature". Journal of Dentistry, Aug. 2006, vol. 34, No. 7, pp. 412-419.
International Search Report for PCT International Application No. PCT/US2014/054074, dated Dec. 11, 2014, 3 pages.

* cited by examiner

*Primary Examiner* — Walter E Webb
(74) *Attorney, Agent, or Firm* — 3M Innovative Properties Compa

(57) ABSTRACT

An oral composition is described. The oral composition can include a solvent having water and a cosolvent chosen from lower alkyl alcohols and acetone; a basic copolymer having basic acrylate monomeric units, basic methacrylate monomeric units, or a combination thereof; no less than 0.5 wt-% of an acid buffering or neutralizing agent; and optionally an active agent. The oral composition can include from about 6° to about 15° wt % of water, from about 30° to about 80° wt % of the cosolvent, and from about 25 to about 55° wt-% of the basic copolymer. The basic copolymer can be dissolved in the oral composition, the oral composition is capable of forming a film on a surface when contacted with an aqueous solution; and the wt-% of each component is based on the total weight of the composition.

20 Claims, No Drawings

(56) References Cited

FOREIGN PATENT DOCUMENTS

| WO | WO 2013-162404 | 10/2013 |
| WO | WO 2015-038376 | 3/2015 |
| WO | WO 2015-038580 | 3/2015 |
| WO | WO 2015-071386 | 5/2015 |
| WO | WO 2015-160762 | 10/2015 |

ORAL COMPOSITIONS

CROSS REFERENCE TO RELATED APPLICATIONS

This is a continuation application of U.S. patent application Ser. No. 14/917,442, filed Mar. 8, 2016, which is a 371 National Stage Entry of International Application No. PCT/US2014/054074, filed Sep. 4, 2014, which claims the benefit of U.S. Provisional Application No. 61/876,441, filed Sep. 11, 2013, the disclosures of which are incorporated by reference herein in their entireties.

FIELD

The present disclosure generally relates to oral compositions, e.g. oral compositions with acid buffering or neutralizing capacity.

BACKGROUND

The erosion of dental enamel can lead to pain, discoloration, mechanical failure, and greater susceptibility to dental carries. Chemical erosion of dental enamel may arise from the presence of acid in the oral cavity. One of the many purposes that oral compositions may serve is to help control pH in the oral cavity.

SUMMARY

One of big concerns in dentistry is acid erosion which is the irreversible loss of dental structure due to chemical dissolution by acids. Some existing strategies of controlling oral pH are to include an alkaline agent in the formulation of an oral care composition. However, these buffer systems do not have high enough buffer capacity to protect against acid based enamel erosion.

The present disclosure generally relates to oral compositions, e.g. oral compositions with acid buffering or neutralization capacity. Generally, the oral composition of the present disclosure has the capability to buffer or neutralizing acid in oral cavity. In addition, the oral composition of the present disclosure can form a film in less than about 30 seconds after the oral composition is contacted with water or dried with a stream of compressed air. As a result, the oral composition of the present disclosure can provide a barrier to protect dental tissues.

Some aspects of the present disclosure provide an oral composition. The oral composition can include a solvent comprising water and a cosolvent chosen from lower alkyl alcohols and acetone; a basic copolymer comprising basic acrylate monomeric units, basic methacrylate monomeric units, or a combination thereof; no less than 0.5 wt-% of an acid buffering or neutralizing agent; and optionally an active agent. The oral composition can include from about 6 to about 15 wt-% of water, from about 30 to about 80 wt-% of the cosolvent, and from about 25 to about 55 wt-% of the basic copolymer. The basic copolymer can be dissolved in the oral composition, the oral composition is capable of forming a film on a surface when contacted with an aqueous solution; and the wt-% of each component is based on the total weight of the composition.

Other features and aspects of the present disclosure will become apparent by consideration of the detailed description and accompanying drawings.

DETAILED DESCRIPTION

Before any embodiments of the present disclosure are explained in detail, it is understood that the invention is not limited in its application to the details of use, construction, and the arrangement of components set forth in the following description or illustrated in the following drawings. The invention is capable of other embodiments and of being practiced or of being carried out in various ways that will become apparent to a person of ordinary skill in the art upon reading the present disclosure. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is understood that other embodiments may be utilized and structural or logical changes may be made without departing from the scope of the present disclosure.

The present disclosure generally relates to oral compositions. Particularly, for example, the oral compositions of the present disclosure can be used to neutralize acids in the oral cavity.

As used herein, dental structures include, but are not limited to, dental tissues and dental articles.

As used herein, dental tissues include, but are not limited to hard and soft dental tissues. Hard and soft oral tissues include, but not limited to, teeth, dental arch, and the surrounding tissues and support structures including gingiva and hard palate.

As used herein, dental articles include, but are not limited to an article that can be attached (e.g., bonded) to an oral surface (e.g., a tooth structure). Examples of dental articles include, but are not limited to, replacements, inlays, onlays, veneers, full and partial crowns, bridges, implants, implant abutments, copings, dentures, posts, bridge frameworks and other bridge structures, abutments, orthodontic appliances and devices including, but not limited to archwires, buccal tubes, brackets and bands, and prostheses (e.g., partial or fill dentures).

As used herein, an aqueous solution includes, but is not limited to water, saliva, artificial saliva or combinations thereof.

In some embodiments, an oral composition is provided. The oral composition can include a solvent, a basic copolymer, an acid buffering or neutralizing agent and optionally an active agent. The solvent can have water and a cosolvent. The cosolvent can be chosen from lower alkyl alcohols and acetone. The basic copolymer can have basic acrylate monomeric units, basic methacrylate monomeric units, or a combination thereof. In some embodiments, the oral composition can comprise no less than 0.5 wt-% of an acid buffering or neutralizing agent. In some embodiments, the oral composition can comprise from about 6 to about 15 wt-% of water, from about 30 to about 80 wt-% of the cosolvent, and from about 25 to about 55 wt-% of the basic copolymer;

The basic copolymer can be dissolved in the oral composition. The oral composition is capable of forming a film on a surface when contacted with an aqueous solution and the wt-% of each component is based on the total weight of the composition.

In some embodiments, the oral composition of the present disclosure can be used to provide coatings that seal open dentin tubules and/or enamel cracks to minimize tooth sensitivity. In some embodiments, the oral composition can comprise from about 8 to about 12 wt-% of the water.

As referred to herein, the lower alkyl alcohols can include low carbon number (e.g. $C_1$-$C_5$) alcohols. Examples of lower alkyl alcohols as used herein include, but are not limited to, ethanol, isopropanol, propylene glycol, glycerin and low molecular weight polyethylene glycol and ethylene glycol based ester alcohols.

In some embodiments, the cosolvent can be ethanol. In other embodiments, the oral composition can comprise from about 35 to 60 wt-% of the cosolvent.

In some embodiments, the solvent can further include at least one additional component chosen from isopropanol, propylene glycol, glycerin, low molecular weight polyethylene glycol, ethylene glycol based ester alcohols, and combinations thereof. In other embodiments, the solvent can include water, ethanol and glycerin.

The basic copolymer, for example, can be used as film formers. When the film is formed, it can, for example, provide a barrier to protect the dental tissues, provide an anchoring structure to the dental tissues, and promote such tissues to enhance uptake active agents. The basic coating also worked as an acid buffer or acid neutralizing composition, since it can react with acid to prevent tooth acid erosion.

In some embodiments, the basic copolymer can include a copolymer containing dimethylaminoethyl methacrylate. In some other embodiments, the basic copolymer can include a copolymer based on dimethylaminoethyl methacrylate, butyl methacrylate, and methyl methacrylate. In other embodiments, the basic copolymer can be chosen from Eudragit E100 and other copolymer containing dimethylaminoethyl methacrylate for ionic crosslinking.

In some embodiments, the molecular weight of the basic copolymer can be from about 10,000 to about 100,000.

In some embodiments, the oral composition of the present disclosure can further include a neutral copolymer having neutral acrylate monomeric units, neutral methacrylate monomeric units, or a combination thereof.

In some embodiments, the neutral copolymer can include copolymers of ethyl acrylate, methyl methacrylate and methacrylic acid ester with quaternary ammonium groups.

In some embodiments, the neutral copolymer can include Eudragit RS100 (marketed by Evonic Industries AG, Damstadt, Germany), Eudragit RL 100 (marketed by Evonic Industries AG, Damstadt, Germany), and combinations thereof.

In some embodiments, the oral composition can comprise from about 0 to about 40 wt-% of the neutral copolymer.

Neutral copolymers can be used as film formers with a flexible property and a low strength that maintain adhesion during scratching or toothbrushing. The flexible neutral copolymers can help to form a tougher film and thus provide a good adhesion to dental tissues. In some embodiments, the consistency of the oral composition of the present disclosure can be from about 45 to about 110. The viscosities of the oral composition are characterized with consistency. The higher the consistency of the composition represents the easier spreading of the composition when pressure is applied, which means lower viscosity. The oral composition has certain consistency range to be applied in an oral cavity. When the consistency of the oral composition is too high, the oral composition is too runny and produces a dropping problem. When the consistency of the oral composition is too low, the oral composition is too viscous and is difficult to spread.

When the oral composition of the present disclosure contacts water, the water miscible solvents can diffuse into water and water can also diffuse into the oral composition. As a result, the molecular interaction among the copolymer chains can increase dramatically and then form a durable, toothbrush abrasion resistant and slippery film. Alternatively, the film can be formed by air drying. For example, air blowing can evaporate water and co-solvents to form the durable, brush abrasion resistant and slippery film.

In some embodiments, the oral composition of the present disclosure can form the film in less than about 30 seconds after the oral composition is contacted with water or dried with a stream of compressed air.

The oral composition of the present disclosure can provide prolonged coating/film. In some embodiments, the film remains on at least 90% of the surface after brushing the surface for at least 5 strokes. In some other embodiments, the film remains on at least 90% of the surface after brushing the surface for at least 10 strokes. In other embodiments, the film remains on at least 90% of the surface after brushing the surface for at least 20 strokes. In yet other embodiments, the film remains on at least 90% of the surface after brushing the surface for at least 30 strokes. In some cases, the film remains on at least 90% of the surface after brushing the surface for at least 60 strokes. In other cases, the film remains on at least 90% of the surface after brushing the surface for at least 90 strokes. In yet other cases, the film remains on at least 90% of the surface after brushing the surface for at least 120 strokes.

In some embodiments, the film remains on at least 90% of the surface after brushing the surface for from 5 to 120 strokes. In some other embodiments, the film remains on at least 90% of the surface after brushing the surface for from 10 to 90 strokes. In other embodiments, the film remains on at least 90% of the surface after brushing the surface for from 20 to 60 strokes. In yet other embodiments, the film remains on at least 90% of the surface after brushing the surface for from 5 to 120 strokes.

In some embodiments, the oral composition can be suitable for administration to the oral cavity of a patient.

Various methods can be employed to apply the oral composition on the dental structure. In some embodiments, the oral composition can be applied from the composition's container or dispenser such as a bottle, syringe, or tube. In some embodiments, a dental brush, microfiber, foam or sponge applicator or cotton Q tip is used to rub the surface of the dental structure and leave a thin layer of coating on the surface. In some other embodiments, a tray applicator, a dental tray, or a dental strip filled with the oral composition can be used. The oral composition can cover the surface of the dental structure and leave a layer of coating on the surface. In other embodiments, the oral composition can be sprayed (e.g. air-brushing) with a spray device or aerosol applicator onto the surface of the dental structure. In other embodiments, the oral composition can be directly painted onto the surface of the dental structure with a brush tip attached to a syringe. In yet other embodiments, the oral composition can be applied as a rinse. The oral composition can be set into a coating on the dental structure and its attachments within 30 seconds by water, saliva, or dried by air blowing.

The oral composition of the present disclosure has the capability to buffer or neutralize acid in oral cavity to reduce acid erosion.

The acid buffering or neutralizing agent of the present disclosure can include any anti-acid compounds suitable for use in the present disclosure. In some embodiments, the acid buffering agent can include any basic substance which dissociates in water (i.e., an aqueous base) to produce one or more hydroxyl ions, or any substance which has can accept a proton, or which has an unshared pair of electrons.

In some embodiments, the acid buffering or neutralizing agent can include carbonates, bicarbonates, chlorides, hydroxides, dibasic citrates phosphates, sulfates and the like, typically in the form of a salt. Exemplary salts include a complex with sodium, potassium, calcium, ammonium, aluminum, magnesium, and the like. In some other embodiments, the acid buffering agent can include sodium carbonate, potassium carbonate, calcium carbonate, ammonium bicarbonate, ammonium carbonate, ammonium chloride, ammonium hydroxide, dibasic ammonium citrate, ammonium phosphate (monobasic or dibasic), ammonium sulfate, aluminum carbonate, aluminum hydroxide, calcium citrate, calcium hydroxide, magnesium carbonate, magnesium hydroxide, magnesium phosphate (dibasic), potassium hydroxide, potassium bicarbonate, and the like.

In some embodiments, the acid buffering or neutralizing agent can include phosphate based buffers which contain $PO_4^{3-}$ anion (e.g., sodium phosphate, potassium phosphate, calcium phosphate and ammonium phosphate), hydrogen phosphate based buffers which contain $HPO_4^{2-}$ anion (e.g., sodium hydrogen phosphate, potassium phosphate and calcium phosphate), dihydrogen phosphaste based buffers which contain $H_2PO_4$ anoin (e.g., sodium dihydrogen phosphate, potassium dihydrogen phosphate and calcium dihydrogen phosphate), carboxylates based buffers which contain $RCOO^-$ anion (e.g., sodium acetate, sodium citrate, potassium acetate, ammonium acetate and ammonium citrate), carbonate based buffers which contain $CO_3^{2-}$ anion (e.g., sodium carbonate, calcium carbonate, magnesium carbonate, iron carbonate, potassium carbonate and ammonium carbonate), hydrogen carbonate buffers which contain $HCO_3^-$ anion (e.g., sodium hydrogen carbonate, calcium hydrogen carbonate, ammonium hydrogen carbonate and potassium hydrogen carbonate).

The oral composition of the present disclosure can release active agents to strengthen the dental tissues and reduce sensitivity. In some embodiments, the oral composition of the present disclosure can include active agents. In other embodiments, the active agents can include, but are not limited to whitening agents, anticaries agents, fluoride-delivery agents, anti-gingivitis agents, tartar control agents, antiplaque agents, periodontal actives, breath freshening agents, malodor control agents, tooth desensitizers, salivary stimulants, flavors, biofilm disruptors, antimicrobials, anesthetic agent, pain killers, stain removal agents, coloring agents, remineralization agents, calculus-softening agents, and combinations thereof.

In various embodiments, the oral compositions of the present disclosure can include a whitening agent. As further discussed below, a "whitening agent" is a material which is effective to effect whitening of a tooth surface to which it is applied. In various embodiments, the oral compositions of the present disclosure can include a peroxide whitening agent, comprising a peroxide compound. As referred to herein, a "peroxide compound" is an oxidizing compound comprising a bivalent oxygen-oxygen group. Peroxide compounds can include, but are not limited to, peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and, alkaline earth metals can include, but are not limited to, lithium peroxide, potassium peroxide, sodium peroxide, magnesium peroxide, calcium peroxide, barium peroxide, and mixtures thereof. Organic peroxy compounds can include, but are not limited to, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts can include, but are not limited to, organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound can include, but are not limited to, hydrogen peroxide, urea peroxide, sodium percarbonate and mixtures thereof. In one embodiment, the peroxide compounds can include hydrogen peroxide. In one embodiment, the peroxide compound can consist essentially of hydrogen peroxide.

The oral compositions of the present disclosure can include a non-peroxide whitening agent. Whitening agents among those useful herein can include non-peroxy compounds, such as chlorine dioxide, chlorites and hypochlorites. Chlorites and hypochlorites can include, but are not limited to, those of alkali and alkaline earth metals such as lithium, potassium, sodium, magnesium, calcium and barium. Non-peroxide whitening agents can also include, but are not limited to, colorants, such as titanium dioxide and hydroxyapatite.

The oral compositions of the present disclosure can include a tartar control (anticalculus) agent. Tartar control agents among those useful herein can include, but are not limited to, phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts can include, but are not limited to, monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents can include, but are not limited to, polycarboxylate polymers and polyvinyl methyl ether/maleic anhydride (PVME/MA) copolymers, such as those available under the Gantrez® from ISP, Wayne, N.J.

The oral compositions of the present disclosure can include a stannous ion source useful, for example, as a periodontal active, tartar control agent, anticaries agent or tooth desensitizer. Any orally acceptable stannous ion source can be used, including, but not limited to, stannous fluoride, other stannous halides such as stannous chloride dehydrate, organic stannous carboxylate salts such as stannous formate, acetate, gluconate, lactate, tartrate, oxalate, malonate and citrate, stannous ethylene glyoxide and the like.

The oral compositions of the present disclosure can include an antimicrobial (e.g., antibacterial) agent. Any orally acceptable antimicrobial agent can be used, including, but not limited to, Triclosan (5-chloro-2-(2,4-dichlorophenoxy)phenol); 8-hydroxyquinoline and salts thereof; zinc and stannous ion sources such as zinc citrate, zinc sulphate, zinc glycinate, sodium zinc citrate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride,); bisguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; magnolia extract; grapeseed extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; and mixtures thereof. A further illustrative list of useful antibacterial agents is described in detail in U.S. Pat. No. 5,776,435, which is incorporated herein by reference.

The oral compositions of the present disclosure can include an antioxidant. Any orally acceptable antioxidant can be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The oral compositions of the present disclosure can include a saliva stimulating agent, useful for example in amelioration of dry mouth. Any orally acceptable saliva stimulating agent can be used, including without limitation food acids such as citric, lactic, malic, succinic, ascorbic, adipic, fumaric, and tartaric acids, and mixtures thereof.

The oral compositions of the present disclosure can include a breath freshening agent. Any orally acceptable breath freshening agent can be used, including without limitation zinc salts such as zinc gluconate, zinc citrate and zinc chlorite, alpha-ionone and mixtures thereof.

The oral compositions of the present disclosure can include an antiplaque (e.g., plaque disrupting) agent. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

In some embodiments, the antiplaque agent can include a compound of general Formula I or a pharmaceutically acceptable salt, thereof:

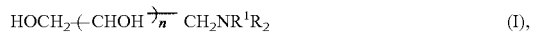

$$HOCH_2\text{--}(CHOH)_n\text{--}CH_2NR^1R_2 \quad (I),$$

wherein $R^1$ and $R^2$ are independently selected from a hydrogen atom, an alkyl group, $C(O)R^3$, and $SO_2R^4$; $R^3$ and $R^4$ are independently selected from an alkyl group, an aryl group, and an aralkyl group; and n is an integer from 2 to 5. In some embodiments, the pharmaceutically acceptable salt is free of unsubstituted or substituted tropolone. In some embodiments, $R^1$ and $R^2$ each comprise a hydrogen atom, or are independently selected from a hydrogen atom and an alkyl group. In certain embodiments, $R^1$ or $R^2$ independently comprise an alkyl group of about one to about ten carbon atoms. In other embodiments, $R^1$ comprises a hydrogen atom and $R^2$ comprises $C(O)R^3$ or $SO_2R^4$. Typically, $R^3$ comprises an alkyl group having from about one to about twenty-six carbon atoms, more typically from about six to about sixteen carbon atoms. A further illustrative list of useful antiplaque agents is described in detail in U.S. Application & Publication No. US2013/0052146, which is incorporated herein by reference.

The oral compositions of the present disclosure can include an anti-inflammatory agent. Any orally acceptable anti-inflammatory agent can be used, including without limitation steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone, and mixtures thereof.

The oral compositions of the present disclosure can include an $H_2$ antagonist. $H_2$ antagonist useful herein include, but not limited to, cimetidine, etintidine, ranitidine, ICIA-5165, tiotidinc, ORF-17578, lupititidinc, donctidinc, famotidinc, roxatidinc, pifatidinc, lamtidine, BL-6548, BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, HB-408.4, and mixtures thereof.

The oral compositions of the present disclosure can include a desensitizing agent. Desensitizing agents useful herein include, but not limited to, potassium citrate, potassium chloride, potassium tartrate, potassium bicarbonate, potassium oxalate, potassium nitrate, strontium salts, arginine and mixtures thereof. Alternatively or in addition a local or systemic analgesic such as aspirin, codeine, acetaminophen, sodium salicylate or triethanolamine salicylate can be used.

The oral compositions of the present disclosure can include a nutrient. Suitable nutrients can include without limitation, vitamins, minerals, amino acids, and mixtures thereof. Vitamins include, but not limited to, Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include, but not limited to, amino acids (such as L-tryptophane, L-lysine, methionine, threonine, levocarnitine and L-carnitine), lipotropics (such as choline, inositol, betaine, and linoleic acid), fish oil (including components thereof such as omega-3 (N-3) polyunsaturated fatty acids, eicosapentaenoic acid and docosahexaenoic acid), coenzyme Q10, and mixtures thereof.

The oral compositions of the present disclosure can include proteins. Suitable proteins can include, but are not limited to, milk proteins and enzymes such as peroxide-producing enzymes, amylase, and plaque-disrupting agents such as papain, glucoamylase, glucose oxidase.

The oral compositions of the present disclosure can include an inorganic or organic fluoride ion source useful, for example, as an anti-caries agent. Any orally acceptable fluoride ion source can be used, including without limitation potassium, sodium and ammonium fluorides and monofluorophosphates, stannous fluoride, indium fluoride and mixtures thereof. Organic fluorides sources can include tetralkylammonium fluoride or tetralkylammonium tetrafluorborate salts and the like. In various embodiments, water-soluble fluoride ion sources are used. In some other embodiments, the active agent can include at least two different fluoride salts. In other embodiments, the active agent can include, but is not limited to, sodium fluoride, strontium fluoride, calcium fluoride, zinc fluoride, calcium chloride, calcium nitrate, calcium phosphates, calcium hydrogen phosphate, calcium dihydrogen phosphate, and combinations thereof. In some embodiments, the active agent can provide a sustained fluoride release for at least 24 hours. As a result, the oral compositions of the present disclosure can, for example, provide a sustained fluoride release in an oral composition.

The following embodiments are intended to be illustrative of the present disclosure and not limiting.

EMBODIMENTS

Embodiment 1 is an oral composition, comprising:
a solvent comprising water and a cosolvent chosen from lower alkyl alcohols and acetone;
a basic copolymer comprising basic acrylate monomeric units, basic methacrylate monomeric units, or a combination thereof;
no less than 0.5 wt-% of an acid buffering or neutralizing agent; and
optionally an active agent;
wherein the oral composition comprises from about 6 to about 15 wt-% of water, from about 30 to about 80 wt-% of the cosolvent, and from about 25 to about 55 wt-% of the basic copolymer;
wherein the basic copolymer is dissolved in the oral composition;
wherein the oral composition is capable of forming a film on a surface when contacted with an aqueous solution; and
wherein the wt-% of each component is based on the total weight of the composition.

Embodiment 2 is the oral composition of embodiment 1, wherein the oral composition further comprises a neutral copolymer comprising neutral acrylate monomeric units, neutral methacrylate monomeric units, or a combination thereof.

Embodiment 3 is the oral composition of any proceeding embodiment, wherein the oral composition from about 0 to about 40 wt-% of the neutral copolymer.

Embodiment 4 is the oral composition of any preceding embodiment, wherein the neutral copolymer is chosen from Eudragit RS100 and Eudragit RL 100.

Embodiment 5 is the oral composition of any preceding embodiment, wherein the basic copolymer is chosen from Eudragit E100 and other copolymer containing dimethylaminoethyl methacrylate for ionic crosslinking Embodiment 6 is the oral composition of any preceding embodiment, wherein the molecular weight of the basic copolymer is from about 10,000 to about 100,000.

Embodiment7 is the oral composition of any preceding embodiment, wherein the oral composition is capable of forming the film in less than about 30 seconds after the oral composition is contacted with water.

Embodiment 8 is the oral composition of any preceding embodiment, wherein the consistency of the oral composition is from about 45 to about 110.

Embodiment 9 is the oral composition of any preceding embodiment, wherein the cosolvent is ethanol.

Embodiment 10 is the oral composition of any preceding embodiment, wherein the solvent further comprises at least one additional component chosen from isopropanol, propylene glycol, glycerin, low molecular weight polyethylene glycol, ethylene glycol based ester alcohols, and combinations thereof.

Embodiment 11 is the oral composition of any preceding embodiment, wherein the oral composition comprises from about 8 to about 12 wt-% of the water.

Embodiment 12 is the oral composition of any preceding embodiment, wherein the oral composition comprises from about 35 to 60 wt-% of the cosolvent.

Embodiment 13 is the oral composition of any preceding embodiment, wherein the acid buffering or neutralizing agent is selected from carbonates, bicarbonates, chlorides, hydroxides, dibasic citrates phosphates, sulfates, and combinations thereof.

Embodiment 14 is the oral composition of any preceding embodiment, wherein the acid buffering or neutralizing agent is selected from phosphate based buffers, hydrogen phosphate based buffers, dihydrogen phosphaste based buffers, carboxylates based buffers, carbonate based buffers, hydrogen carbonate buffers, and combinations thereof.

Embodiment 15 is the oral composition of any preceding embodiment, wherein the active agent is selected from whitening agents, anticaries agents, fluoride-delivery agents, anti-gingivitis agents, tartar control agents, antiplaque agents, periodontal actives, breath freshening agents, malodor control agents, tooth desensitizers, salivary stimulants, flavors, biofilm disruptors, antimicrobials, anesthetic agent, pain killers, stain removal agents, coloring agents, remineralization agents, calculus-softening agents, and combinations thereof.

Embodiment 16 is the oral composition of any preceding embodiment, wherein the active agent is a fluoride composition.

Embodiment 17 is the oral composition of any preceding embodiment, wherein the active agent provides a sustained fluoride release for at least 24 hours.

Embodiment 18 is the oral composition of any preceding embodiment, wherein the active agent comprises at least two different fluoride salts.

Embodiment 19 is the oral composition of any preceding embodiment, wherein the active agent is chosen from sodium fluoride, strontium fluoride, calcium fluoride, zinc fluoride, calcium chloride, calcium nitrate, calcium phosphates, calcium hydrogen phosphate, calcium dihydrogen phosphate, and combinations thereof.

Embodiment 20 is the oral composition of any preceding embodiment, wherein the film remains on at least 90% of the surface after brushing the surface for at least 5 strokes.

Embodiment 21 is the oral composition of any preceding embodiment, wherein the film remains on at least 90% of the surface after brushing the surface for at least 10 strokes.

Embodiment 22 is the oral composition of any preceding embodiment, wherein the film remains on at least 90% of the surface after brushing the surface for at least 20 strokes.

Embodiment 23 is the oral composition of any preceding embodiment, wherein the film remains on at least 90% of the surface after brushing the surface for at least 30 strokes.

Embodiment 24 is the oral composition of any preceding embodiment, wherein the film remains on at least 90% of the surface after brushing the surface for at least 60 strokes.

Embodiment 25 is the oral composition of any preceding embodiment, wherein the film remains on at least 90% of the surface after brushing the surface for at least 90 strokes.

Embodiment 26 is the oral composition of any preceding embodiment, wherein the film remains on at least 90% of the surface after brushing the surface for at least 120 strokes.

Embodiment 27 is the oral composition of any preceding embodiment, wherein the film remains on at least 90% of the surface after brushing the surface for from 5 to 120 strokes.

Embodiment 28 is the oral composition of any preceding embodiment, wherein the film remains on at least 90% of the surface after brushing the surface for from 10 to 90 strokes.

Embodiment 29 is the oral composition of any preceding embodiment, wherein the film remains on at least 90% of the surface after brushing the surface for from 20 to 60 strokes.

Embodiment 30 is the oral composition of any preceding embodiment, wherein the film remains on at least 90% of the surface after brushing the surface for from 5 to 120 strokes.

The following working examples are intended to be illustrative of the present disclosure and not limiting.

EXAMPLES

Objects and advantages of this invention are further illustrated by the following examples, but the particular materials and amounts thereof recited in these examples, as well as other conditions and details, should not be construed to unduly limit this invention.

The materials used to prepare examples of the invention (Ex) as well as comparative examples (CE) are outlined below.

Materials

| Material | Description | Source |
|---|---|---|
| EUDRAGIT RS100 | Neutral copolymer of ethyl acrylate, methyl methacrylate and a low content of methacrylic acid ester with quaternary ammonium groups. | Evonic Industries, Darmstadt, Germany |
| EUDRAGIT RL100 | Neutral copolymer of ethyl acrylate, methyl methacrylate and a low content of methacrylic acid ester with quaternary ammonium groups | Evonic Industries, Darmstadt, Germany |
| EUDRAGIT E100 | Basic cationic copolymer based on dimethylaminoethyl methacrylate, butyl methacrylate, and methyl methacrylate | Evonic Industries, Darmstadt, Germany |
| EtOH | Ethanol, 200 proof, USP grade | Columbus Chemical Industries, Columbus, WI |
| PPG | Propylene glycol, USP grade | EMD Billerica, MA |
| Glycerol | USP grade | Sigma-Aldrich, St Louis, MO |
| NaF | milled sodium fluoride (passed through 30 micro screen) | 3M ESPE, St Paul, MN |
| $K_3PO_4$ | Potassium Phosphate Tribasic | J T Baker Phillipsburg, NJ |
| NaCl | Sodium chloride | EMD Billerica, MA |
| $Ca_2Cl_2 \cdot 2H_2O$ | Calcium chloride | EMD Billerica, MA |
| KCl | Potassium chloride | EMD Billerica, MA |
| Gastric Mucin | Sigma porcine stomach mucin type II | Sigma Aldrich |
| $KH_2PO_4$ | Potassium dihydrogen phosphate | J T Baker Phillipsburg, NJ |
| NaOH | Sodium hydroxide | Alfa Aesar |
| $CaCO_3$ | Calcium carbonate | EMD Billerica, MA |
| $Na_2CO_3$ | Sodium carbonate | VWR, Radnor, PA |
| $K_3PO_4$ | Potassium phospahte | Alfa Aesar, Ward Hill, MA |
| Arginine | | Alfa Aesar, Ward Hill, MA |
| Hydrogenated rosin | Foral AX-E hydrogenated rosin | Eastman, Kingsport, TN |
| Lauric acid | | TCI, Portland, OR |
| Stearic acid | | TCI, Portland, OR |
| Octanic aicd | | Alfa Aesar, Ward Hill, MA |
| pH paper | Color pHast pH 6.5-10.0 | EM science, Gibbstown, NJ |

Preparation of Coating Compositions

Polymer solutions were prepared by first weighing the designated amount of solvent into a 250 ml jar that has a cap. The designated amount of polymer material was then added to the jar. The jar was sealed and then placed on a Wheaton Culture Roller for 2-3 days (~30rpm) until the polymer was completely dissolved in the solvent. Additional ingredients such as NaF, other salts, viscosity modifiers, flavorings, etc. were added to the polymer solution using two 2 minute cycles in a speed mixer (SpeedMixer DAC150.1 FVZ available from FlacTek, Inc., Landrum, S.C.) set at 3000 rpm. The materials used in each coating composition as well as the amount (in grams) are shown in the examples and tables below.

Preparation of Artificial Saliva

Artificial saliva was prepared with following procedure: 3.52 g of gastric mucin, 0.610 g NaCl, 0.341 g $CaCl_2.2H_2O$, 1.183 g $KH_2PO_4$ and 1.179 g KCL were weighed into a 2000 ml flask. 1600 ml of deionized (DI) water was slowly added using a magnetic stir bar to mix solution until all solids are dissolved. The pH was adjusted to 7.0 with 50% NaOH solution.

Test Methods

Coating Evaluation—Feel, Set, Adhesion and Abrasion Resistance Test

Compositions of the invention and comparative compositions were coated onto a glass (or plastic if noted) slide (available from VWR, Radnor Pa.) or bovine teeth using a cotton swab or small brush. The coated substrate what then dipped into a container of tap water for 30 seconds at room temperature (~25° C.). The coating was then qualitatively evaluated to determine if a film had formed ("set"). Additionally the set films were evaluated at to their adhesion to the substrate. Adhesion was deemed "good" when the set film could not be pushed away by finger pressure and "no" when the set film could be pushed away by finger pressure. Abrasion resistance was evaluated by brushing the set coating with a tooth brush and counting the number of brush strokes required to remove the coating.

Fluoride Release Test

Approximately 40-50 mg of coating composition was evenly painted onto a 1 inch×1 inch plastic slide (Rinzyl plastic micro slide available from VRW, Radnor, Pa.). The coated slide was immersed in 25 ml of deionized water in a plastic test tube for 1 hour. After 1 hour, the slide was removed, rinsed and immersed in a second 25 ml aliquot of water in another test tube. After 3 more hours (4 hours total), the process was repeated and the slide was immersed in a third 25 ml aliquot of water. After 2 more hours (6 hours total) the process was again repeated and the slide was place in a fourth 25 ml aliquot of water where it remained for an additional 18 hours (24 hours total) before being removed. Each of 25 ml aliquots of deionized water were then evaluated for fluoride concentration. 10 ml of the samples solutions from above preparation were mixed with 10 ml of TISAB II to make the solution for fluoride concentration measurements. The fluoride concentrations were measured using a Cole Parmer fluoride ion meter equipped with a fluoride combination electrode which had been standardized using standard concentrations of fluoride buffered with TISAB II. Five replicate samples were run to get an average. The fluoride concentration was measured in parts per million and the fluoride release was reported as $\mu gF/cm^2$ coating using the following equation.

$$\mu gF/cm^2 \text{ coating} = \frac{(\text{Concentration of F in ppm}) * (\text{sample volume in mL})}{(\text{coating area in cm}^2)}$$

Abrasion Resistance Tooth Brush Testing

Bovine teeth were potted in a poly(methyl)methacrylate (PMMA) resin and then polished with 320 grit sandpaper to expose the enamel surface. The exposed enamels were wiped with paper tower to remove excess of water, then coated with about 10 mg materials to form a thin layer on enamel, and then stored in 37° C. artificial saliva for varying amounts of time. A tooth brush machine (available from Foth Production Solution, LLC, Greenbay Wis.) was used to test coating wear durability on enamel. Tooth brush head was cut from tooth brush with brand name Acclean gentle care from Henry Schein and inserted into the fixture on the tooth brush machine. The potted bovine teeth were inserted and fixed in a plastic port filled with brush media. The tooth brush head was rest on the coating surface. The machine can control the tooth brush head moving back and forth against the coating on enamel. The brushing stroke is defined as brushing the surface back and forth one time. 5 ml of 1:1 water and tooth paste (CREST cavity protection tooth paste) mixture was used as brush media. After certain brushing strokes, the coating surfaces were checked and the amount of wear was estimated.

pH Measurement

The pH of the coating solutions was determined using pH paper.

Examples 1-5 and Comparative Examples 1-4:
Compositions with Additives and Fluoride Release Oral (coating) compositions were prepared and coated as described above using the materials and amounts (in grams) as outlined in Table 1 below. Coated films were evaluated for set, adhesion and fluoride release as described above.

TABLE 1

|  | Ex 1 | Ex 2 | Ex 3 | Ex 4 | Ex 5 | CE 1 | CE 2 | CE 3 | CE 4 |
|---|---|---|---|---|---|---|---|---|---|
| Lauric acid | 10 | 0 | 0 | 8 | 8 | 0 | 0 | 17 | 10 |
| Stearic acid | 0 | 0 | 0 | 0 | 0 | 31 | 0 | 10 | 18 |
| Octanic aicd | 0 | 0 | 0 | 0 | 0 | 0 | 22 | 0 | 0 |
| Ethanol | 40 | 40 | 40 | 40 | 40 | 35 | 35 | 35 | 35 |
| DI water | 10 | 10 | 10 | 10 | 10 | 4 | 4 | 4 | 4 |
| Hydrogenated rosin | 0 | 15 | 0 | 0 | 0 | 0 | 0 | 0 | 0 |
| EUDRAGIT E100 | 40 | 35 | 50 | 42 | 42 | 30 | 39 | 34 | 34 |
| Polymer solution | yes | yes | yes | yes | yes | no | yes | no | no |
| TCP | 0.5 | 0.5 | 0.5 | 0.5 | 0.5 | — | — | — | — |
| NaF | 5.0 | 5.0 | 5.0 | 5.0 | 5.0 | — | — | — | — |
| Set in water | yes | yes | yes | yes | yes | — | no | — | — |
| Film adhesion | good | good | good | good | good | — | no | — | — |
| Accumulative Fluoride Release 1 hr | 151.2 | 84.4 | 76.0 | 150.8 | 118.6 | — | — | — | — |
| Accumulative Fluoride Release 4 hr | 153.2 | 139.5 | 130.2 | 152.1 | 119.8 | — | — | — | — |
| Accumulative Fluoride Release 6 hr | 153.4 | 152.9 | 146.2 | 152.4 | 119.9 | — | — | — | — |
| Accumulative Fluoride Release 24 hr | 153.7 | 166.9 | 177.4 | 152.5 | 120.2 | — | — | — | — |

Examples 6-10: Coating Compositions with Various Polymers and Fluoride Release

Coating compositions were prepared and coated as described above using the materials and amounts (in grams) as outlined in Table 2 below. Coated films were evaluated for set, adhesion and fluoride release as described above.

TABLE 2

|  | Ex 6 | Ex 7 | Ex 8 | Ex 9 | Ex 10 |
|---|---|---|---|---|---|
| Lauric acid | 6 | 0 | 0 | 0 | 0 |
| Ethanol | 40 | 45.2 | 45.2 | 45.2 | 45.2 |
| DI water | 10 | 11.3 | 11.3 | 11.3 | 11.3 |
| EUDRAGIT RS100 | 0 | 0 | 0 | 5.2 | 5.2 |
| EUDRAGIT RL100 | 6 | 5.2 | 5.2 | 0 | 0 |
| EUDRAGIT E100 | 38 | 38.3 | 38.3 | 38.3 | 38.3 |
| Polymer solution | yes | yes | yes | yes | yes |
| $SrF_2$ | 0 | 0 | 1.5 | 0 | 1.5 |
| TCP | 0.5 | 0.5 | 0.5 | 0.5 | 0.5 |
| NaF | 5.0 | 5.0 | 4.0 | 5.0 | 4.0 |
| Set in water | yes | yes | yes | yes | yes |
| Film adhesion | good | good | good | good | good |
| Accumulative Fluoride Release 1 hr | 153.1 | 114.7 | 96.1 | 105.8 | 78.7 |
| Accumulative Fluoride Release 4 hr | 155.9 | 144.6 | 121.3 | 148.8 | 120.5 |
| Accumulative Fluoride Release 6 hr | 156.1 | 147.3 | 125.6 | 156.4 | 127.6 |
| Accumulative Fluoride Release 24 hr | 156.6 | 152.6 | 132.6 | 163.1 | 135.2 |

Examples 11-19 and Comparative Example 5: Compositions with Various Solvents

Coating compositions were prepared and coated as described above using the materials and amounts (in grams) as outlined in Table 3 below. The pH of the coating composition was determined as described above and the coated films were evaluated for set and adhesion.

TABLE 3

|  | Ex 11 | Ex 12 | Ex 13 | Ex 14 | Ex 15 | Ex 16 | Ex 17 | CE 5 | Ex 18 | Ex 19 |
|---|---|---|---|---|---|---|---|---|---|---|
| Ethanol | 40 | 40 | 40 | 40 | 40 | 35 | 30 | 25 | 35 | 30 |
| DI water | 15 | 15 | 15 | 15 | 10 | 10 | 10 | 10 | 10 | 10 |
| PPG | 0 | 0 | 0 | 0 | 0 | 0 | 0 | 0 | 10 | 15 |
| Glycerin | 0 | 0 | 0 | 0 | 5 | 10 | 15 | 20 | 0 | 0 |
| EUDRAGIT RL100 | 5 | 15 | 0 | 25 | 5 | 5 | 5 | 5 | 5 | 5 |
| EUDRAGIT E100 | 40 | 30 | 45 | 20 | 40 | 40 | 40 | 40 | 40 | 40 |
| Polymer solution | yes | yes | yes | yes | yes | yes | yes | no | yes | yes |
| Set in water | yes | yes | yes | yes | yes | yes | yes | — | yes | yes |
| Film adhesion | good | good | good | good | good | good | good | — | good | good |
| pH | 8.1 | 8.1 | 8.3 | 7.9 | 8.1 | 8.1 | 8.1 | NA | 8.1 | 8.1 |

Example 20-27: Coating Compositions with Alkaline Additives

Coating compositions were prepared and coated as described above using the materials and amounts (in grams) as outlined in Table 4 below. The coated films were evaluated for set, adhesion and fluoride release as described above.

The pH of the coating compositions outlined in Table 4 was determined using pH paper as described above. Coatings were then prepared as described above by placing about 25 mg of coating composition on a 2.5 cm×2.5 cm square glass slide and then dipping the coated slide into tap water for 30 seconds to form a hard film. The coated slides were removed from the tap water and then dipped into 100 ml of water that was adjusted to pH 4 with a trace amount of 37% phosphoric acid. After 10 seconds the coated slides were removed from the acid adjusted water and the pH of the acid adjusted water on the wet coated surface was determined using pH paper. The results of this buffering test are shown in Table 4 below.

TABLE 4

|  | Ex 20 | Ex 21 | Ex 22 | Ex 23 | Ex 24 | Ex 25 | Ex 26 | Ex 27 |
|---|---|---|---|---|---|---|---|---|
| Ethanol | 40 | 40 | 40 | 40 | 40 | 40 | 40 | 40 |
| DI water | 15 | 15 | 15 | 15 | 15 | 15 | 15 | 15 |
| EUDRAGIT RL100 | 5 | 5 | 5 | 5 | 5 | 5 | 5 | 5 |
| EUDRAGIT E100 | 40 | 40 | 40 | 40 | 40 | 40 | 40 | 40 |
| $CaCO_3$ | 0 | 0 | 0 | 0 | 0 | 2 | 2 | 2 |
| $Na_2CO_3$ | 0 | 0 | 0 | 2 | 2 | 0 | 0 | 0 |
| $K_3PO_4$ | 2 | 2 | 0 | 2 | 0 | 0 | 2 | 2 |
| Arginine | 0 | 2 | 2 | 0 | 2 | 2 | 2 | 0 |
| TCP | 0.15 | 0.15 | 0.15 | 0.15 | 0.15 | 0.15 | 0.15 | 0.15 |
| NaF | 5.0 | 5.0 | 4.0 | 4.0 | 4.0 | 4.0 | 4.0 | 4.0 |
| Set in water | yes | yes | yes | yes | yes | yes | yes | yes |
| Film adhesion | good | good | good | good | good | good | good | good |
| Accumulative Fluoride Release 1 hr | 55.9 | 94.9 | 111.1 | 77.7 | 127.1 | 99.51 | 93.4 | 69.6 |
| Accumulative Fluoride Release 4 hr | 130.7 | 158.7 | 156.2 | 140.0 | 172.7 | 120.4 | 140.9 | 115.7 |
| Accumulative Fluoride Release 6 hr | 151.3 | 167.9 | 163.4 | 150.8 | 176.6 | 122.5 | 145.8 | 120.3 |
| Accumulative Fluoride Release 24 hr | 176.2 | 175.3 | 174.7 | 159.6 | 179.4 | 125.2 | 151.4 | 128.2 |
| pH of coating composition | 9 | 9 | 8.7 | 9.5 | 9.5 | 8.7 | 9.5 | 9.5 |
| pH of acid treated water on coated substrate | 8.1 | 8.1 | 7.1 | 8.1 | 8.1 | 7.1 | 8.1 | 8.1 |

Example 6 and 7: Abrasion Resistance

The abrasion resistance on bovine teeth of coating composition of Ex 6 and 7 was determined as described above. Three replicate samples of coated teeth were soaked in 37° C. artificial saliva for either 3 hours or 24 hours and then subjected to brushing. The amount of coating removed after a specific number of brush strokes is reported in Table 5 below.

TABLE 5

| Example | Tooth # | 37 C. artificial saliva for 3 hrs | | | | 37 C. artificial saliva for 24 hrs | | | |
|---|---|---|---|---|---|---|---|---|---|
| Ex 6 | strokes | 10 | 30 | 60 | 90 | 10 | 30 | 60 | 90 |
|  | 1 | 90% | — | — | — | 90% | — | — | — |
|  | 2 | 90% | — | — | — | 90% | — | — | — |
|  | 3 | 90% | — | — | — | 90% | — | — | — |
| Ex 7 | strokes | 30 | 60 | 90 | 120 | 30 | 60 | 90 | 120 |
|  | 1 | 0% | 10% | 30% | 50% | 0% | 0% | 10% | 50% |
|  | 2 | 0% | 30% | 50% | 90% | 0% | 10% | 30% | 90% |
|  | 3 | 0% | 10% | 30% | 50% | 0% | 0% | 10% | 50% |

What is claimed is:

1. A method of sealing open dentin tubules, the method comprising:
   Forming a coating on the open dentin tubules with
   an oral composition comprising:
   a solvent comprising water and a cosolvent chosen from lower alkyl alcohols and acetone;
   a basic copolymer comprising basic acrylate monomeric units, basic methacrylate monomeric units, or a combination thereof;
   no less than 0.5 wt-% of an acid buffering or neutralizing agent; and
   optionally an active agent;
   wherein the oral composition comprises from about 6 to about 15 wt-% of water, from about 30 to about 80 wt-% of the cosolvent, and from about 25 to about 55 wt-% of the basic copolymer;
   wherein the basic copolymer is dissolved in the oral composition;
   wherein the oral composition is capable of forming a film on a surface when contacted with an aqueous solution; and
   wherein the wt-% of each component is based on the total weight of the composition.

2. The method of claim 1, wherein the step of forming a coating on the open dentin tubules comprises applying the oral composition to a dental structure.

3. The method of claim 2, wherein the step of applying the oral composition to the dental structure comprises use of a dental brush, microfiber, foam or sponge applicator.

4. The method of claim 3, wherein use of a dental brush, microfiber, foam or sponge applicator comprises rubbing the surface of the dental structure.

5. The method of claim 4, wherein rubbing the surface of the dental structure leaves a thin layer of a coating of the oral composition on the surface of the dental structure.

6. The method of claim 2, wherein the step of applying the oral composition to the dental structure comprises use of a tray applicator, a dental tray, or a dental strip filled with the oral composition.

7. The method of claim 2, wherein the step of applying the oral composition to the dental structure comprises spraying the oral composition onto the surface of the dental structure.

8. The method of claim 7, wherein spraying the oral composition onto the surface of the dental structure comprises use of an air-brush, a spray device or an aerosol applicator.

9. The method of claim 2, wherein the step of applying the oral composition to the dental structure comprises painting the oral composition onto the surface of the dental structure.

10. The method of claim 9, wherein painting the oral composition onto the surface of the dental structure comprises use of a brush tip attached to a syringe.

11. The method of claim 2, wherein the step of applying the oral composition to the dental structure comprises use of a rinse comprising the oral composition.

12. The method of claim 1, wherein the oral composition further comprises a neutral copolymer comprising neutral acrylate monomeric units, neutral methacrylate monomeric units, or a combination thereof.

13. The oral composition of claim 12, wherein the oral composition comprises from about 0 to about 40 wt-% of the neutral copolymer.

14. The method of claim 12, wherein the neutral copolymer is chosen from Eudragit RS100 and Eudragit RL 100.

15. The method of claim 1, wherein the molecular weight of the basic copolymer is from about 10,000 to about 100,000.

16. The method of claim 1, wherein the cosolvent is ethanol.

17. The method of claim 1, wherein the oral composition comprises from about 8 to about 12 wt-% of the water.

18. The method of claim 1, wherein the oral composition comprises from about 35 to 60 wt-% of the cosolvent.

19. The method of claim 1, wherein the acid buffering or neutralizing agent is selected from carbonates, bicarbonates, chlorides, hydroxides, dibasic citrates phosphates, sulfates, and combinations thereof.

20. The method of claim 1, wherein the active agent is selected from whitening agents, anticaries agents, fluoride-delivery agents, anti-gingivitis agents, tartar control agents, antiplaque agents, periodontal actives, breath freshening agents, malodor control agents, tooth desensitizers, salivary stimulants, flavors, biofilm disruptors, antimicrobials, anesthetic agent, pain killers, stain removal agents, coloring agents, remineralization agents, calculus-softening agents, and combinations thereof.

* * * * *